(12) United States Patent
Impiö et al.

(10) Patent No.: US 7,152,470 B2
(45) Date of Patent: Dec. 26, 2006

(54) METHOD AND OUTFIT FOR MEASURING OF ACTION OF MUSCLES OF BODY

(75) Inventors: Jussi Impiö, Tampere (FI); Tapio Karinsalo, Kankaanpää (FI); Akseli Reho, Kankaanpää (FI); Arto Remes, Kuopio (FI); Pekka Tolvanen, Kuopio (FI); Elina Välimäki, Tampere (FI)

(73) Assignees: Mega Elektroniikka Oy, Kuopio (FI); Suunto Oy, Vantaa (FI)

( * ) Notice: Subject to any disclaimer, the term of this patent is extended or adjusted under 35 U.S.C. 154(b) by 0 days.

(21) Appl. No.: 11/024,260

(22) Filed: Dec. 27, 2004

(65) Prior Publication Data
US 2005/0178201 A1   Aug. 18, 2005

Related U.S. Application Data

(63) Continuation of application No. PCT/FI2003/00517, filed on Jun. 26, 2003.

(30) Foreign Application Priority Data
Jun. 27, 2002   (FI) ................................. 20021265

(51) Int. Cl.
*A61B 5/22* (2006.01)
(52) U.S. Cl. .................................................. 73/379.01
(58) Field of Classification Search ............ 73/379.01; 600/595, 587; 607/2; 84/687
See application file for complete search history.

(56) References Cited

U.S. PATENT DOCUMENTS 3,704,339 A * 11/1972 Niinomi .................... 84/687
5,112,296 A * 5/1992 Beard et al. ................ 602/28
5,562,707 A * 10/1996 Prochazka et al. .......... 607/2
5,749,365 A    5/1998 Magill ..................... 128/671
5,846,210 A * 12/1998 Ogawa et al. ............. 600/585
6,381,482 B1   4/2002 Jayaraman et al. ........ 600/388
6,428,490 B1 *  8/2002 Kramer et al. ............. 600/595
2001/0041846 A1 11/2001 Appel .......................... 600/546

FOREIGN PATENT DOCUMENTS

WO    WO 90/14792    12/1990

\* cited by examiner

*Primary Examiner*—Jewel Thompson
(74) *Attorney, Agent, or Firm*—Harrington & Smith, LLP

(57) ABSTRACT

The present invention relates to a method and an outfit for measuring of action of muscles of body, in which method electrical signals created by active muscles are measured with a measuring device and a response from action of muscles is given with a response device with a signal perceptible to a user. In the method in accordance with the invention electrical signals of muscles at various points of the body and/or limbs are measured with one or more measuring devices attached and connected to one or more outfits, the functioning of various muscles is monitored and the information is processed in measuring devices. In the outfit in accordance with the invention there are one or more measuring devices integrated for measuring the electrical signals created by the muscles, for monitoring the action, for processing the information, and the outfit includes a response device for giving response.

12 Claims, 7 Drawing Sheets

METHOD AND OUTFIT FOR MEASURING OF ACTION OF MUSCLES OF BODY

This application is a continuation of International Patent Application No. PCT/FI2003/00517 filed Jun. 26, 2003.

The present invention relates to a method for measuring of action of muscles of body, in which method electrical signals created by active muscles are measured with a measuring device and a response from action of muscles is given with a signal perceptible to a user. In addition, the invention relates to an outfit for applying the method.

BACKGROUND OF THE INVENTION

It is recognized to measure the action of muscles of body with various measuring devices. EMG-sensors with which the electrical activity of muscles is monitored and which are placed on a muscle are typical measuring devices. These sensors are placed and fixed usually on a muscle with some suitable attaching means, such as with a tape, belt and so on. It is usual to monitor the active functioning of a muscle/muscles and at the same time give a response with various devices/in various ways, such as with a visual signal, sound, with a signal based on sense of feeling and so on. Usually these response devices are placed at a certain distance from the measuring devices. Many times these response devices are a part of a bigger whole such that training and physical exercise must be carried out in a certain space. A response device may also refer to a separate, portable device, to which the information from sensors is transmitted.

Information and an immediate response from a training or physical exercise performance is effectively attained with present methods during the training/physical exercise, but often the problem is to have and to present the information and/or response the whole time without separate devices in any place regardless of circumstances and/or the place. In addition, in many sports simultaneous information about muscles in various sides of the body and/or limbs and especially the symmetric muscles is required and by means of present devices this information is not available.

Sensors of measuring devices are usually spotlike electrodes about 1 cm by diameter. Sensors are placed on the muscle to be monitored, whereupon EMG-signal as clear as possible is tried to gain and, on the other hand, mistakes and disturbance of adjacent muscles are tried to be avoided. Therefore, sensors are to be placed with extreme accuracy to ensure the reliability, repeatability and comparability of measurements. In addition, sensors may come off or move from their place due to physical exercise performance or perspiration.

Methods of response of present devices are typically numerical or bar graphs based on light (LED or LCD), in which there is a simple scale and, in addition, there may also be a sound response. This kind of a structure requires the device to be placed within the visual field of the trainee or the trainee is to direct his gaze separately to the display of the device. The utilization of the sound response requires relatively soundless application surroundings. These types of responses may cause practical problems in various physical exercise performances and may hinder concentration to the performance itself. Displays based on light are, in addition, all the time on using electricity, and therefore the batteries of the device are unnecessary big or their change period is short.

The load of muscles having influence on the movements of a limb to various its directions has a relation other than balance, which is based on the anatomy of the limb and the biomechanical movements of the limb. For example, for straightening of an elbow the extensor of brachii is used and, correspondingly, for flexing the biceps is used. The work carried out by these muscles naturally differs from each other and, furthermore, the optimal value of the relation in question may vary remarkably depending on sport and physical exercise event. For example, in cross-country skiing the extensor of brachii ("push with a stick") is loaded relatively more than the biceps, which, for its part, is loaded more in rowing ("pull with an oar"). The presentation of these kind of relations requires regulable pair difference, which present devices do not posses.

The purpose of the invention is to provide a method and an outfit, with the use of which disadvantages related to present measurements are eliminated. Particularly, the purpose of the invention is to provide a method and an outfit, which enables the monitoring and getting of a response from a physical exercise the whole time quickly, reliably and simply. Furthermore, the purpose of the invention is to provide a method, which simultaneously gathers information and enables the monitoring of muscles in various sides of body and/or limbs, and especially symmetric muscles.

DESCRIPTION OF THE INVENTION

In the method in accordance with the invention electrical signals of muscles at various points of the body and/or limbs are measured with one or more measuring devices attached and connected to one or more outfits, the functioning of various muscles is monitored and the information is processed in measuring devices. By means of the method the trainee gets immediately response of the balance and the change in balance of actions of muscles, by means of which the trainee may control and improve the efficiency of the physical exercise and prevent the weakening of efficiency due to unilateral fatigue of muscles. Information is processed by computing and analysing functions of the measuring device of the outfit.

In an advantageous application of the invention differences in actions of symmetric muscles in various sides of the body and the limbs during various performances are measured with one or more measuring devices. At that time muscles of the weaker side may be developed in order to improve the sport performance or to return the normal efficiency after an injury.

In the next advantageous additional application of the invention the action of muscles having influence on movements to opposite directions of the same limb and the right relation of their muscular strength is measured. At that time cooperation of muscles having influence on the movement of a limb or a joint may be developed according to each sport in order to achieve maximum use of strength and/or as good as possible endurance of performance.

In the next advantageous additional application of the invention the notable difference of actions of muscles and/or the relation of performed work is indicated to the user by means of response devices attached to the outfit. Too big difference of sides of symmetric muscles, that is the difference of actions and/or action of muscles, muscular strength and the relation of muscular work is indicated by a response device attached to the outfit, such as a light (LED), vibrating device (eccentric motor), sound device or some other recognized response device applicable for is purpose. The response method is chosen on grounds of sport and according to application such that it is explicit and simple and, on the other hand, as little as possible hindering the performance itself as indicated in the next examples. LED lights are placed in both legs or sleeves or corresponding places in an outfit in such a place that they are directed to the trainee's visual field and they are easy to be noticed. For example, LED lights are place to both knees of cycling shorts, which lights are in that case directed to the visual field of the cyclist. In this case, for example, in cycling a smaller load on the left leg is indicated by a LED light placed on the left knee and the load of the right leg muscles, correspondingly, by a LED light on the other knee. A response based on light may not be presented to a runner while running without hindering the performance. When there are vibrating devices instead of LED lights on running shorts, the response of the side difference is given using, for example, a vibrator on the weaker leg.

In the next advantageous additional application of the invention the notable difference in actions of muscles and/or the relation of work carried out is indicated to user by one or more response devices outside the outfit. The user may freely place the response device to a desired point on his body or to some other suitable place near the user, for example, to a handbar of a bicycle or to a gym apparatus. There is a transmitter part in a data processing module, by means of which transmitter the response to be given to the user is transmitted to the response device either via a separate wire or wirelessly. A response device may also be a part of some other device the user is carrying with him or which is placed near the user, such as a wrist computer or some other data processing device. The information to be given to the user as response may be presented by the equipment and the methods in the device itself, such as a display, buzzer, speakers or headphones. The content of the information may consist of numeric or graphic information, visual animation or video picture, signals or speech or combination of all these.

In the next advantageous additional application of the invention the magnitude of significant side difference is regulated or defined in accordance with individual needs and/or in accordance with sport. The magnitude of the significant difference of sides depends on the physical exercise and the physical condition, goals of the trainee and/or other things connected with the trainee. Since a response is given only when the deviation of muscles is greater than the regulated difference of sides the performance of the user is not disturbed with unnecessary information and at the same time battery capacity of the device is saved.

In the next advantageous additional application of the invention a whole group of muscles is measured with the measuring device. A muscle group to be measured is chosen in accordance with a sport such that the work carried out by a muscle group in question corresponds as completely as possible to the whole work carried out by that limb and to which work the muscle group has influence during the performance. Since the electrodes acting as measuring devices have been shaped and situated such that the whole muscle group is measured instead of measuring of an individual muscle little changes in the position of electrodes have no significant effect on the measuring accuracy. While wearing an outfit the electrodes are not always situated exactly on a certain muscle which is not even necessary while wearing the outfit in accordance with the invention, while the main purpose is to compare the whole work carried out by limbs and not the work of individual muscles.

There is one or more measuring devices integrated into the outfit in accordance with the invention for measuring electrical signals caused by muscles, monitoring the functioning, processing information, and the outfit includes a response device for giving response. Since the needed equipment is always situated on the outfit or in close vicinity of the user or such that the user is able to observe the response often enough during the performance, the measurements, follow-up and the response may be carried out the whole time in real time.

In an advantageous application of the invention there are textile electrodes, data processing module, conducting wires made of conducting textile and one or more response module integrated into the outfit. Earlier recognized electrodes and conducting wires suitable for the purpose are employed as textile electrodes and textile conducting wires. Also other kind of electrodes may be employed in other applications. Electrodes, conducting wires and connections on outfits are washable and wear-proof.

In the next additional application of the invention textile electrodes, conducting wires made of conducting textile, data processing module are integrated to the outfit but one or more response devices are situated outside the outfit. The user may freely place the response device in a desired place such that it hinders as little as possible the performance itself. In this case the user observes the response easier and information may be presented more illustratively and reliably.

In an advantageous additional application of the invention there are pockets or corresponding on the outfit to which modules may be removably placed and there are connecting pas corresponding to each other on the outfit and the modules. There are standard connection surfaces on the outfits and the modules such that the same modules may be employed in several different outfits. Wear and tear of an outfit and changing the parts to another outfit enables a long-term use of the same modules and decreases costs.

In an advantageous additional application of the invention there is a uniform large earth connection electrode surface placed on the outfit, the wires from electrodes have been integrated to earth connection. The uniform earth connection surface minimizes the number of earth wires needed to one and, on the other hand, the earth connection point is placed as close as possible to every muscle/muscle group to be measured. The large earth connection electrode surface secures a good contact also while moving. The earth connection functions, at the same time, as a disturbance protection for conductors coming from electrodes.

Typical objects for use of the invention are, for example, the use of the left and right thigh muscle in various sports, such as in cycling, running, skiing, jumping events, strength training, weight lifting and so on.

The method and the outfit may be used for various purposes. Generally, the method and the device are well applicable for monitoring sport performances and enhancing efficiency. In addition, they may be used for rehabilitation of difference in sides of muscles due to injury or for learning of normal courses of a limb by means of muscle strength of right magnitude.

In various sports muscles connected to or needed in those are strained by training. With the method in accordance with the invention various muscle groups and/or various actions are monitored depending on the sport. Next various sports are presented as examples, but the methods in accordance with the invention may, naturally, be applied also in other sports.

In cycling the balance between the left leg and the right leg is tried to be taken care of. The measurings are carried out by taking the mean over regulable time or for the time of a chosen number of cycles of pedals. In addition, the right relation of the extensor and the flexor muscles of knee is monitored targeting to "circle" the pedals instead of "treading" the pedals thus obtaining more even power transmission from pedals to chains and, on the other hand, minimizing the becoming fatigue of muscles of the front side of thighs.

Also in running the balance between the left leg and the right leg is tried to be taken care of. The measurings are carried out by taking the mean over regulable time or for the time of a chosen number of stepping. In addition, the relation of the extensor and the flexor muscles of knee is monitored targeting to a long, low and efficient running step.

In training in gymnastics/in gym/in muscle training the balance between chosen left and right side muscles is monitored as well as the right relation of chosen extensors and flexors. In addition, also other muscle groups such as abdominal/dorsum muscles, with which the posture and the balance of body are maintained, are monitored.

In jumping events the balance between both legs (thighs, calves and so on), for example, in take-off with both feet together is monitored, and in taking off with one leg, the cooperation of muscle pairs having influence in extending and flexing the knee and the lower leg is monitored. In throwing events the relations of work carried out by extensors/flexors of legs and arms and/or dorsum/abdominal muscles having influence on torsion of the body are compared.

Ball games include various exercises and measurements. In football, for example, it is of importance to measure the difference between the kicking strength and the kicking technique of the left leg and the right leg. In addition, by means of the method it is possible to compare the efficiency and the performance technique of turns to the left and to the right in ice hockey, for example.

In rehabilitation the rehabilitating of a limb, put in plaster or operated, into balance with the healthy limb is monitored.

DESCRIPTION OF THE DRAWINGS

Next, the invention will be explained in more detail with reference to the accompanying drawings, in which.

FIG. 1 illustrates the location of the electrodes, conducting wires and the display/vibration unit on the cycling shorts 1. In the figure the cycling shorts are presented on a user. A measuring device, which include measuring electrodes 3, an earth connection electrode 7, a data processing module 5 and a response module 2 presented with dashed lines, are integrated to cycling shorts. The electrodes 3 are, in this case, placed at the point of thigh muscle group on the leg of shorts and the measuring point somewhat above the knee. The electrodes are electrodes, which measure EMG-signals of the muscle group. There are two pairs of electrodes on the front side and two pairs on the backside of the shorts. The pairs are placed symmetrically with each other. The electrodes have been connected to the data processing module with conducting wires 4 and it has been connected to the response module with other conducting wires. On the front side of the shorts, on both sides of the shorts, there is a response module 2 in a pocket, which module in this application is a signal device based on light. The electrodes are so called textile electrodes and the conducting wires have been made of conducting textile material.

FIG. 2 illustrates the connection of the shorts and the data processing module in the back pan of the shorts in more detail. A data processing module 5 has been presented in FIG. 8. A pocket 6 has been made on the waist of the shorts, in the bottom of which pocket there is a connecting area, where the press-stud connections 8 are placed in a standardized order. The counter parts 9 of the press-studs are placed in the bottom or on the side of the data processing module 5, by means of which counter parts the module may be attached to shorts thus connecting it to electrodes and response modules in them. There is also a closable flap at the point of the module in the shorts such that the module is placed in a protective pocket. The module may be removed while desired for washing up of the outfit, for example.

FIG. 3 illustrates the connection of the shorts and the response module in the front part of the cycling shorts in more detail. FIG. 9, for its part, illustrates a LED response module 2 and below, as another application, a vibrating module. FIG. 2 illustrates pockets with flaps 10 made to the legs of the shorts and LED modules 2 placed in them. There are press-stud connections 8 also in this case in the bottom of the pockets for plus and minus contacts.

In accordance with FIG. 9 there are press-stud connections 9 on one side of the modules, with which connections they are connected to the press-stud connections of the outfit. On the opposite side there is the response member, in the first module a light 17 and in the other an eccentric motor, which causes such vibrations that, the user may sense it. In FIG. 3 the LED module is placed in the pocket such that the light is placed at the point of an opening or corresponding in the pocket such that the user may easily notice it.

FIG. 4 illustrates the location of electrodes 3 in cycling shorts and the wirings 4 in more detail. The electrodes have been located on the legs of shorts at the same points in both legs. There are electrodes on the front side and on the backside of the shorts. The conducting wires 11 to LED modules 2 are located separately from the electrode wires 4 in order to minimize disturbances. The conducting wires have been situated to seams on the front side, such that they do not cause chafing between a saddle and skin. The common earth connection 7 to all electrodes is led under the module to the sides of both thighs.

FIG. 5 illustrates the structure of earth connection electrode 7 in cycling shorts in more detail. In the figure there is also the wire tunnel 12, where the conducting wires from measuring electrodes have been placed. The conducting wires from electrodes 3 have been connected in abovementioned manner to the data processing module in accordance with FIGS. 2 and 8, where the common earth connection electrode as well as connections to LED are situated.

In FIGS. 6 and 7 the structure of the wire tunnel has been presented in more detail. In FIG. 6 the wire tunnel has been presented parts separately from each other for the sake of clarity and in FIG. 7 the real structure has been presented. In accordance with FIGS. 6 and 7 the wire tunnel 12 is placed against the skin 16 and in the structure of the outfit there is, from below upwards, the ear connection electrode 7, conducting wires 4 to the measuring electrodes, the conducting network 13, which forms the disturbance protection together with the earth connection electrode, the dry gel 14 improving the electrical contact as well as the shorts material 15.

Figure 1:
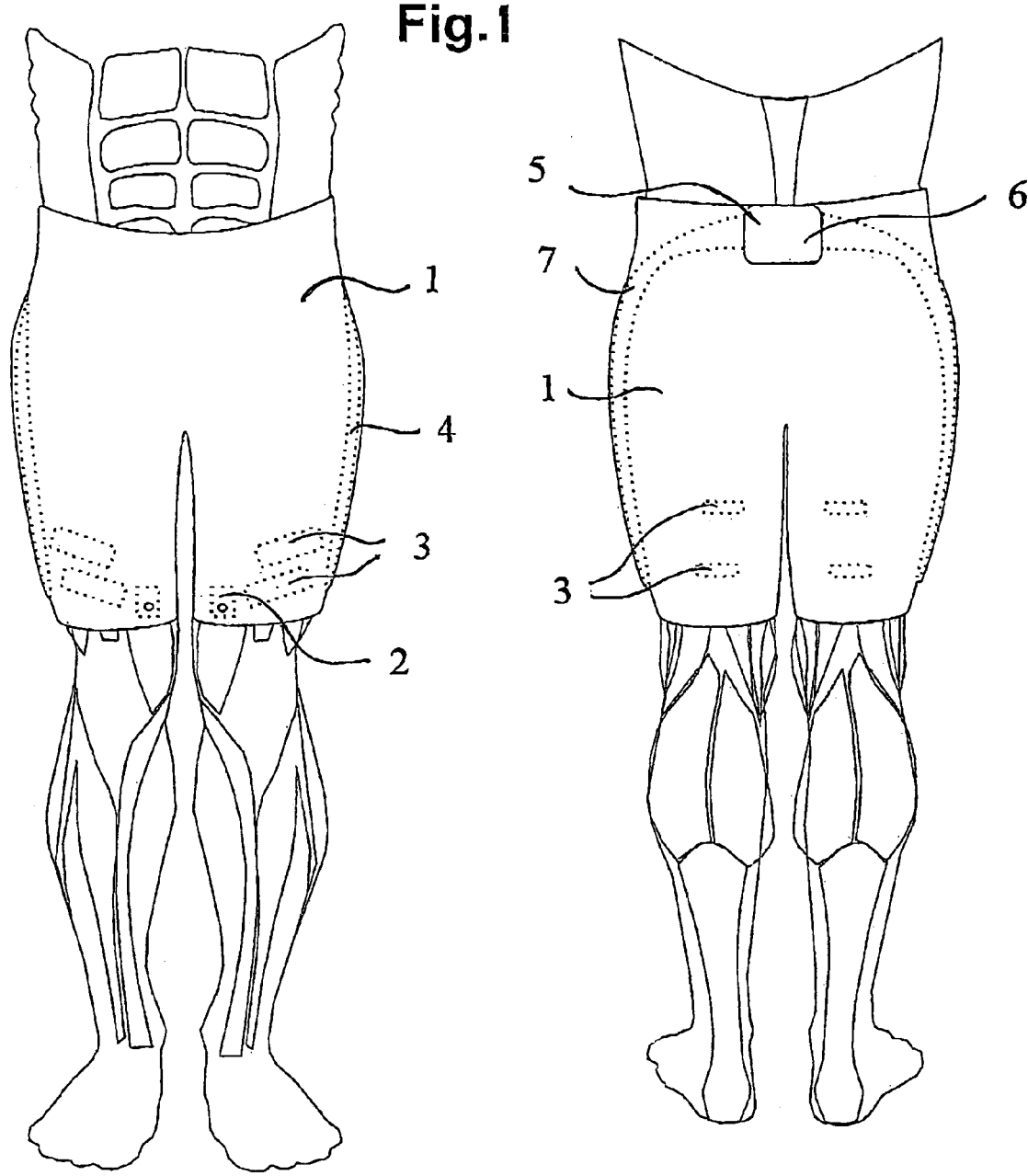
FIG. 1 illustrates an outfit in accordance with the invention viewed from the front and the behind.
Figure 2:
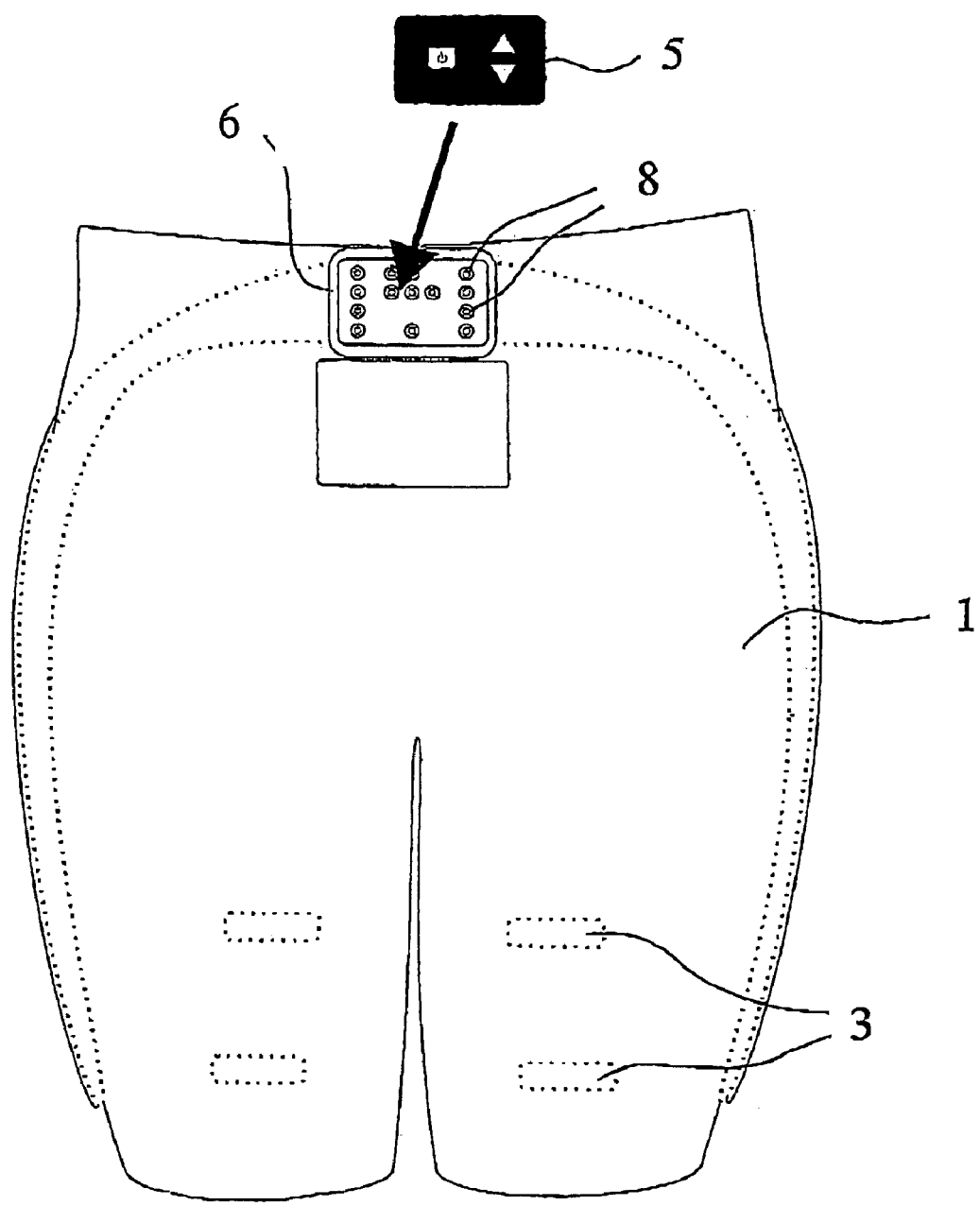
FIG. 2 illustrates a detail of the outfit in accordance with FIG. 1.
Figure 3:
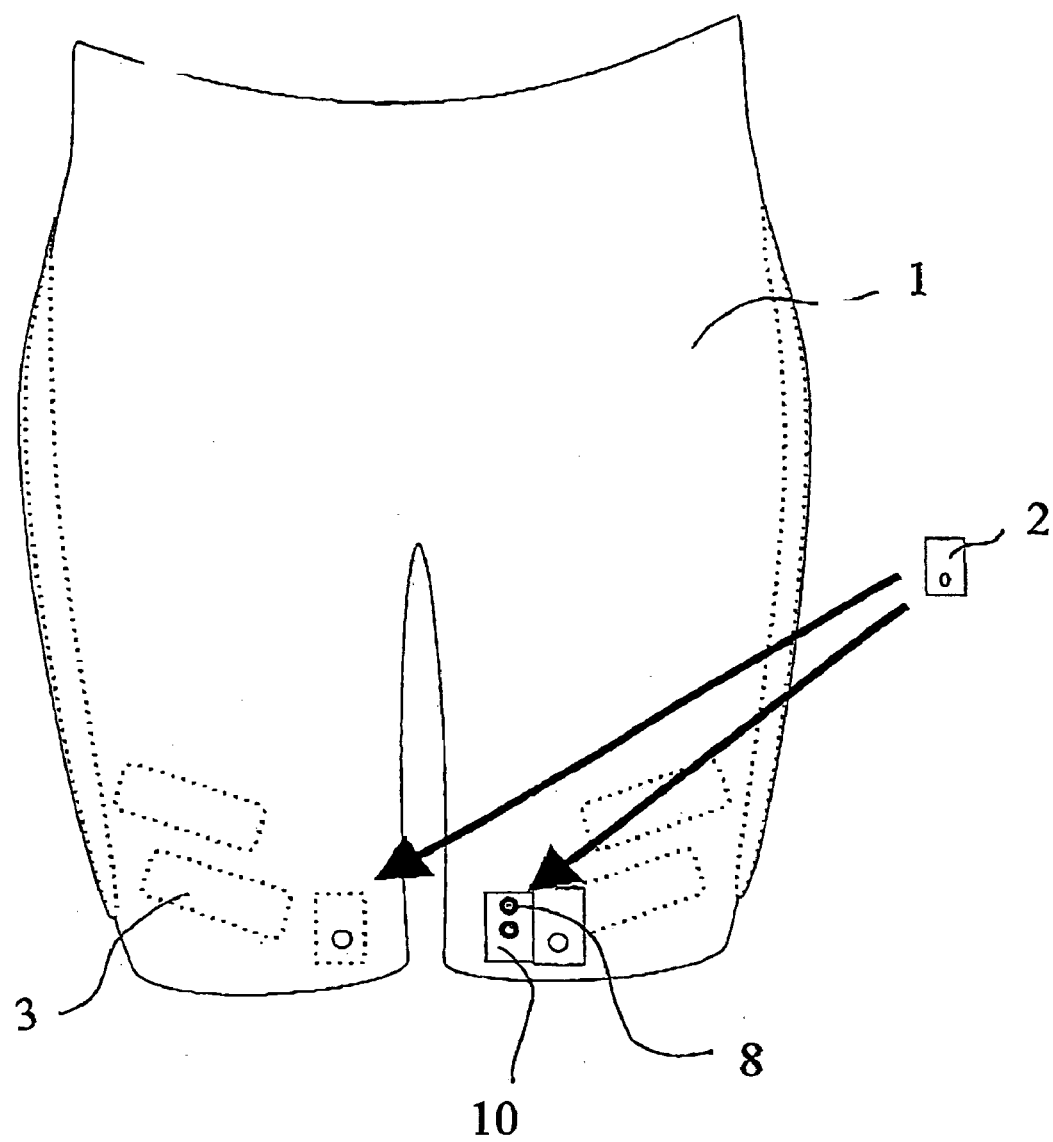
FIG. 3 illustrates another detail of the outfit in accordance with FIG. 1.
Figure 4:
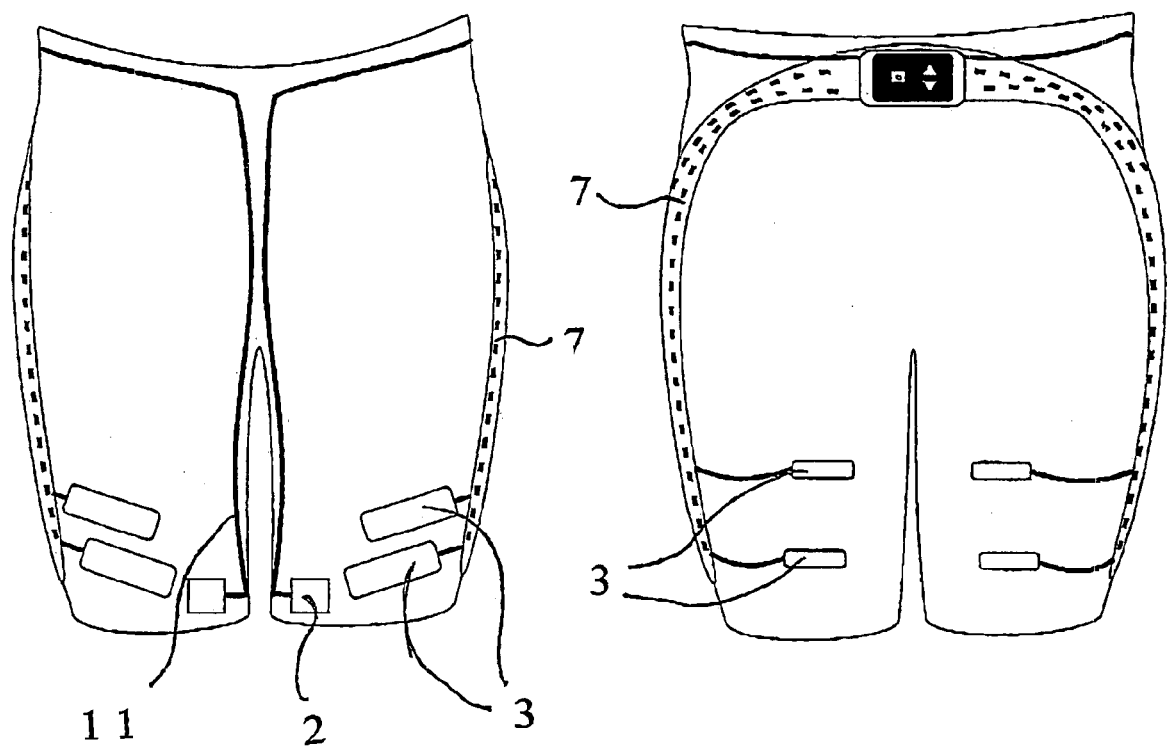
FIG. 4 illustrates the location of electrodes and conducting wires in the outfit in accordance with FIG. 1.
Figure 5:
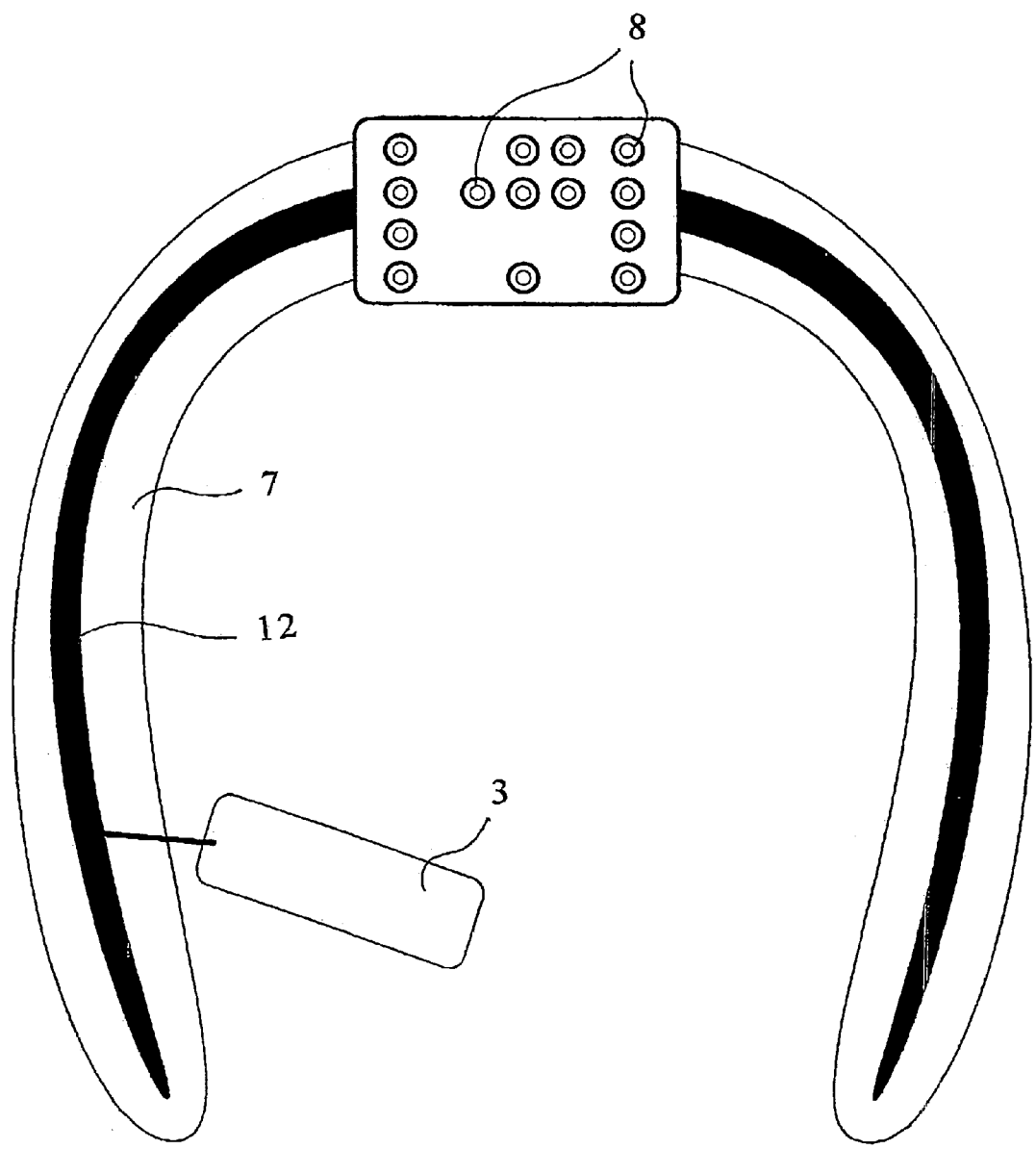
FIG. 5 illustrates a detail of the structure of the outfit in accordance with FIG. 1
Figure 6:
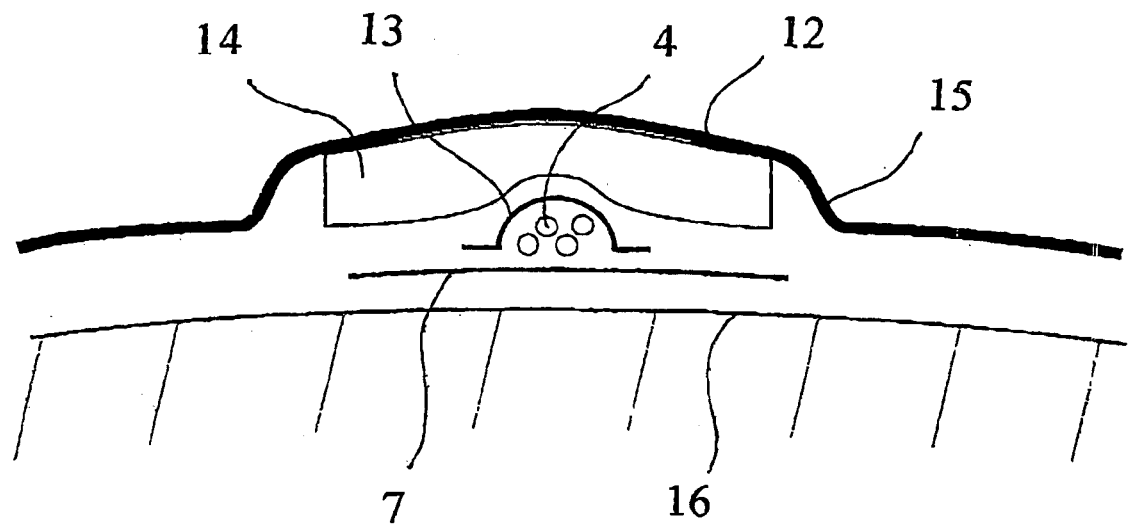
FIGS. 6 and 7 illustrate the structure of the earth connection electrode and the wire tunnel employed in the outfit in accordance with FIG. 1 as a cross-section.
Figure 7:
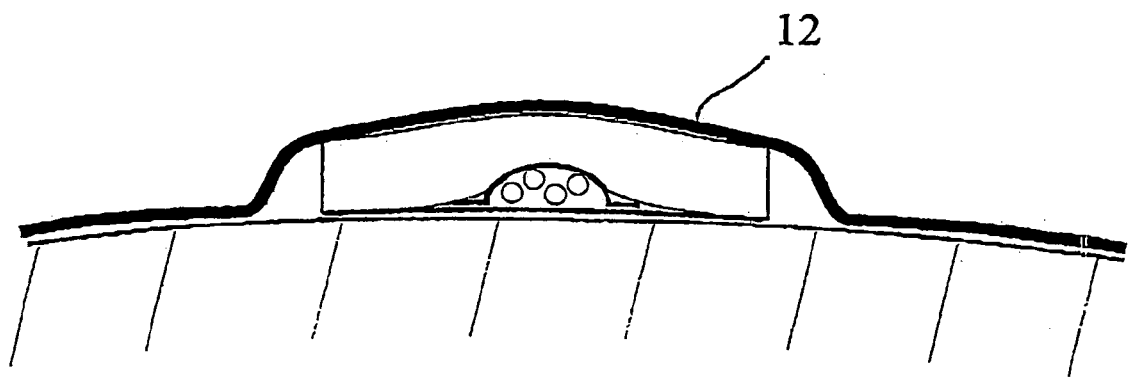
Figure 8:
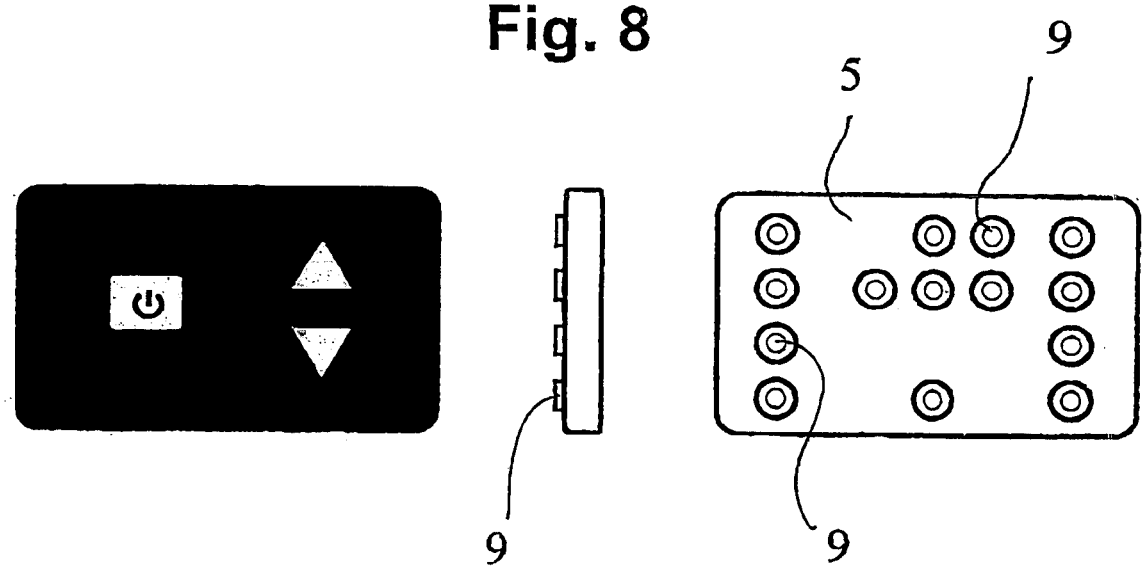
FIG. 8 illustrates a data processing module employed in the outfit in accordance with the invention viewed from various sides.
Figure 9:
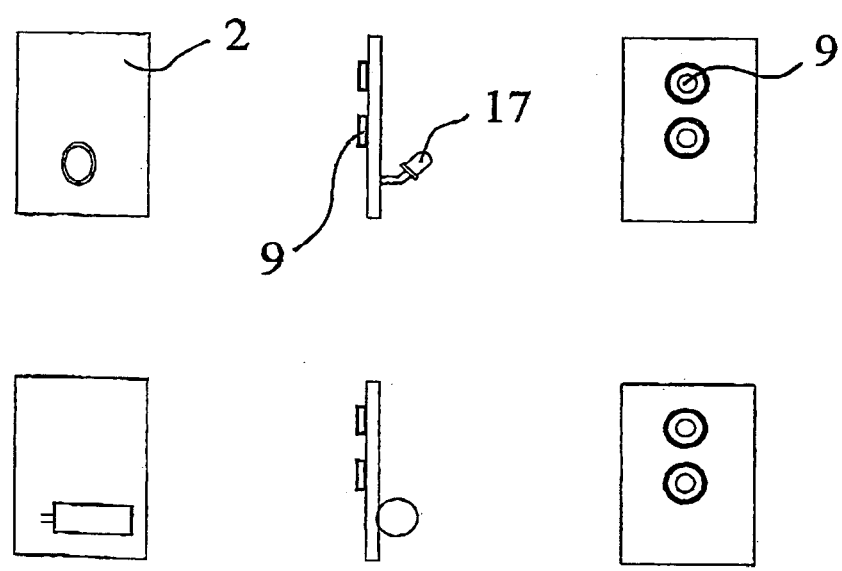
FIG. 9 illustrates two applications of the response module employed in the outfit viewed from various sides.

The structure of the outfit in accordance with the invention may vary in various applications. Various outfits are used in various sports and, therefore, the structure, shape and the location of electrodes depend on the sports and training performance as well on what muscle groups are desired to be observed and monitored.

In one application the data processing module is placed straight on the observed muscle group and connected to electrodes at that point without separate conducting wires.

In an advantageous application the response module and/or its functions have been connected/transmitted straight to the data processing module in which case there is no need for a separate response module.

In some applications of the invention the response device is situated outside the outfit, and it may be attached removably to the outfit, body or to parts of it, such as to the limbs, or it may be attached to some suitable place in close vicinity of the user and the outfit such that the user may observe it. The response device may be integrated to a sports equipment or to a performance place or to the surrounding area. It is, naturally, also possible to place at least one response device at a distance from the user, by the running track next to a sports field, or to a suitable place in a gym, for example. There may also be several response devices in use, in which case at least a part of them may be used, for example, to give information to several users simultaneously and for saving and processing information. Information from the measuring device on the outfit to the response device is transmitted in earlier recognized manner as such making use of wired or wireless data transmitting.

The invention is not limited to the presented advantageous applications but it can vary within the frames of the idea of the invention formed in the claims.

The invention claimed is:

1. A method for measuring of action of muscles of a body, in which electrical signals, such as EMG-signals, created by active muscles are measured with a measuring device and a response from the action of the muscles is given with a response device with a signal perceptible to a user, wherein the electrical signals of the muscles at various points of the body and/or limbs are measured with the measuring device attached and connected to one or more outfits, wherein action of various muscles is monitored and compared, wherein information is processed in the measuring device, and wherein response of the actions and/or comparison of the actions of different muscles is given by the response device.

2. A method in accordance with claim 1 wherein differences in actions of symmetric muscles in various sides of the body and/or the limbs of the left and the right sides during various performances are measured.

3. A method in accordance with claim 1 wherein the action of muscles having influence on movements to opposite directions of the same limb and the right relation of their muscular strength and muscular work carried out are measured.

4. A method in accordance with claim 1, in which noticeable difference in muscle action and/or the relation of work carried out is indicated to user with the response device on the outfit.

5. A method in accordance with claim 1, in which noticeable difference in muscle action and/or the relation of work carried out is indicated to the user with a the response device outside the outfit.

6. A method in accordance with claim 1, in which noticeable magnitude of the difference in actions of symmetric muscles in various sides of the body and/or the limbs of the left and the right sides and/or the relation of work carried out is regulated or defined in accordance with individual needs and/or in accordance with a sport.

7. A method in accordance with claim 1, in which a whole muscle group is measured with the measuring device.

8. An outfit including one or more measuring devices integrated to the outfit for measuring of electrical signals caused by muscles, wherein the measuring device is integrated to the outfit for measuring of EMG-signals caused by the muscles, for monitoring the action of the muscles and for comparing the actions of the muscles on the base of the electrical signals and for processing information from the electrical signals, and wherein the outfit includes a response device for giving a response.

9. An outfit in accordance with claim 8 including textile electrodes, conducting wires made of conducting textile, a data processing module, and one or more response modules integrated to the outfit.

10. An outfit in accordance with claim 8 including textile electrodes, conducting wires made of conducting textile, a data processing module integrated to the outfit, and in which the response device is outside the outfit.

11. An outfit in accordance with claim 9 including pockets on the outfit, to which the modules are removably placed, and that in the outfit and the modules there are connection parts corresponding to each other.

12. An outfit in accordance with claim 8 including a large common earth connection electrode surface placed in the outfit, and that the conducting wires from the electrodes have been integrated to the earth connection.

* * * * *